(12) United States Patent
Maschke et al.

(10) Patent No.: US 7,749,168 B2
(45) Date of Patent: Jul. 6, 2010

(54) MEDICAL SYSTEM FOR EXAMINATION OR TREATMENT

(75) Inventors: Michael Maschke, Lonnerstadt (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 389 days.

(21) Appl. No.: 10/989,167

(22) Filed: Nov. 15, 2004

(65) Prior Publication Data

US 2005/0113685 A1 May 26, 2005

(30) Foreign Application Priority Data

Nov. 21, 2003 (DE) .................. 103 54 496

(51) Int. Cl.
*A61B 8/14* (2006.01)

(52) U.S. Cl. ...................... 600/467; 600/476

(58) Field of Classification Search .......... 600/473, 600/459, 443, 916, 447, 448, 449, 437, 407, 600/408, 467, 476; 128/916
See application file for complete search history.

(56) References Cited

U.S. PATENT DOCUMENTS

| | | | |
|---|---|---|---|
| 5,830,145 A * | 11/1998 | Tenhoff | 600/463 |
| 6,217,527 B1 * | 4/2001 | Selmon et al. | 600/585 |
| 6,416,492 B1 * | 7/2002 | Nielson | 604/22 |
| 6,546,271 B1 | 4/2003 | Reisfeld | |
| 2002/0049375 A1 | 4/2002 | Strommer et al. | |
| 2002/0077546 A1 | 6/2002 | Aldefeld et al. | |
| 2002/0103430 A1 * | 8/2002 | Hastings et al. | 600/411 |
| 2003/0082105 A1 * | 5/2003 | Fischman et al. | 424/9.6 |
| 2003/0160721 A1 * | 8/2003 | Gilboa et al. | 342/450 |
| 2003/0176786 A1 | 9/2003 | Maschke | |
| 2007/0066890 A1 * | 3/2007 | Maschke | 600/424 |
| 2007/0066983 A1 * | 3/2007 | Maschke | 606/159 |
| 2007/0135712 A1 * | 6/2007 | Maschke | 600/433 |
| 2007/0135886 A1 * | 6/2007 | Maschke | 623/1.11 |

FOREIGN PATENT DOCUMENTS

| | | |
|---|---|---|
| EP | 0 776 176 B1 | 6/1997 |
| EP | 0 885 594 A2 | 12/1998 |
| WO | WO 01/11409 A2 | 2/2001 |

* cited by examiner

*Primary Examiner*—Brian Casler
*Assistant Examiner*—Elmer Chao

(57) ABSTRACT

Medical examination and/or treatment system having a catheter (1) with a sensor (3, 4) connected to an image recording system, said sensor being connected to an image processing unit (24, 25) for evaluating the sensor signals recorded in an examination area, a display unit (26) for displaying the images (12) of the image processing unit (24, 25) and a means for detecting the position and/or orientation of the catheter tip, whereby the system can generate three-dimensional images from the two-dimensional images (12) of the image recording system based on the detected position and/or direction of the catheter tip.

22 Claims, 3 Drawing Sheets

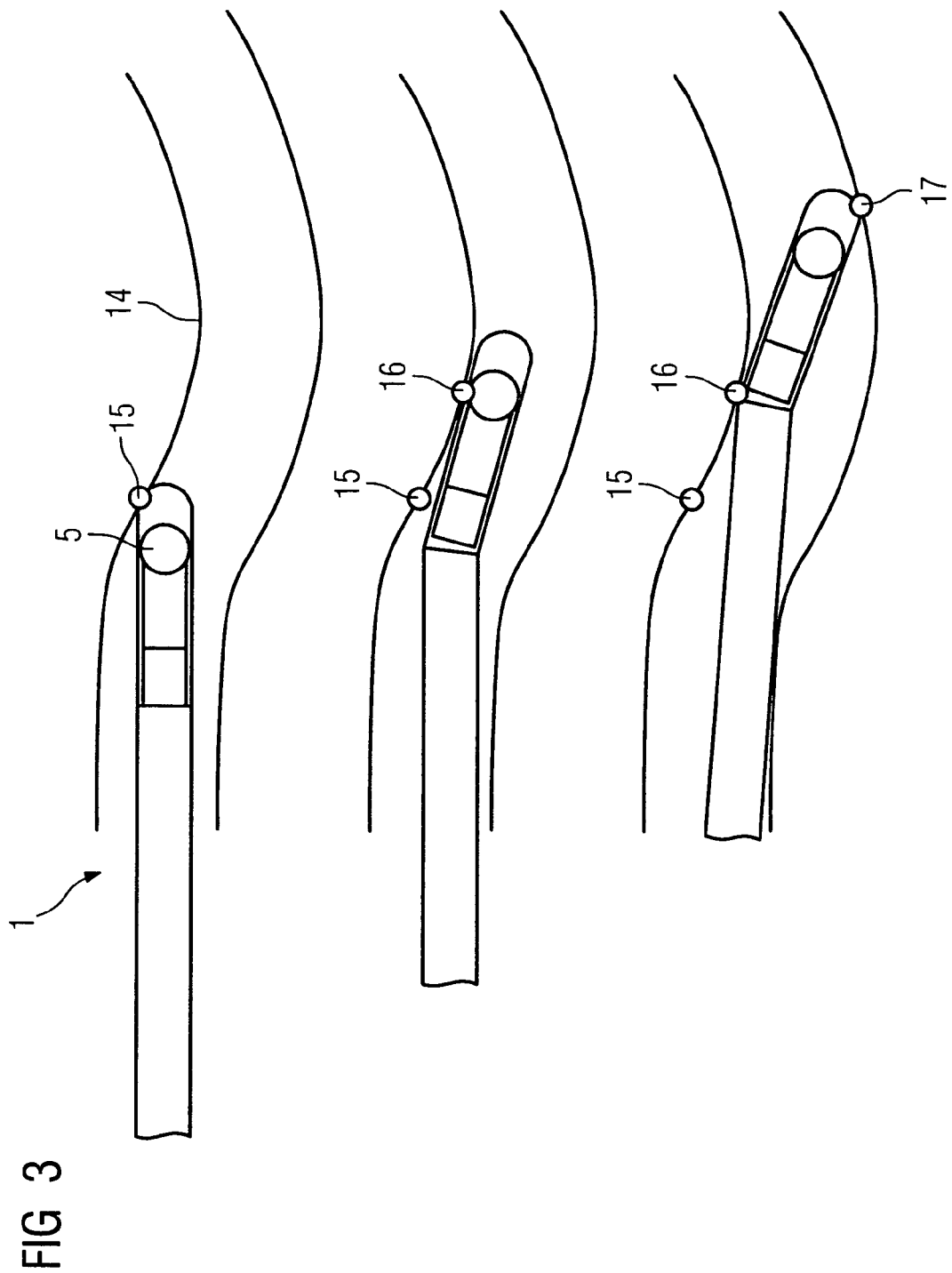

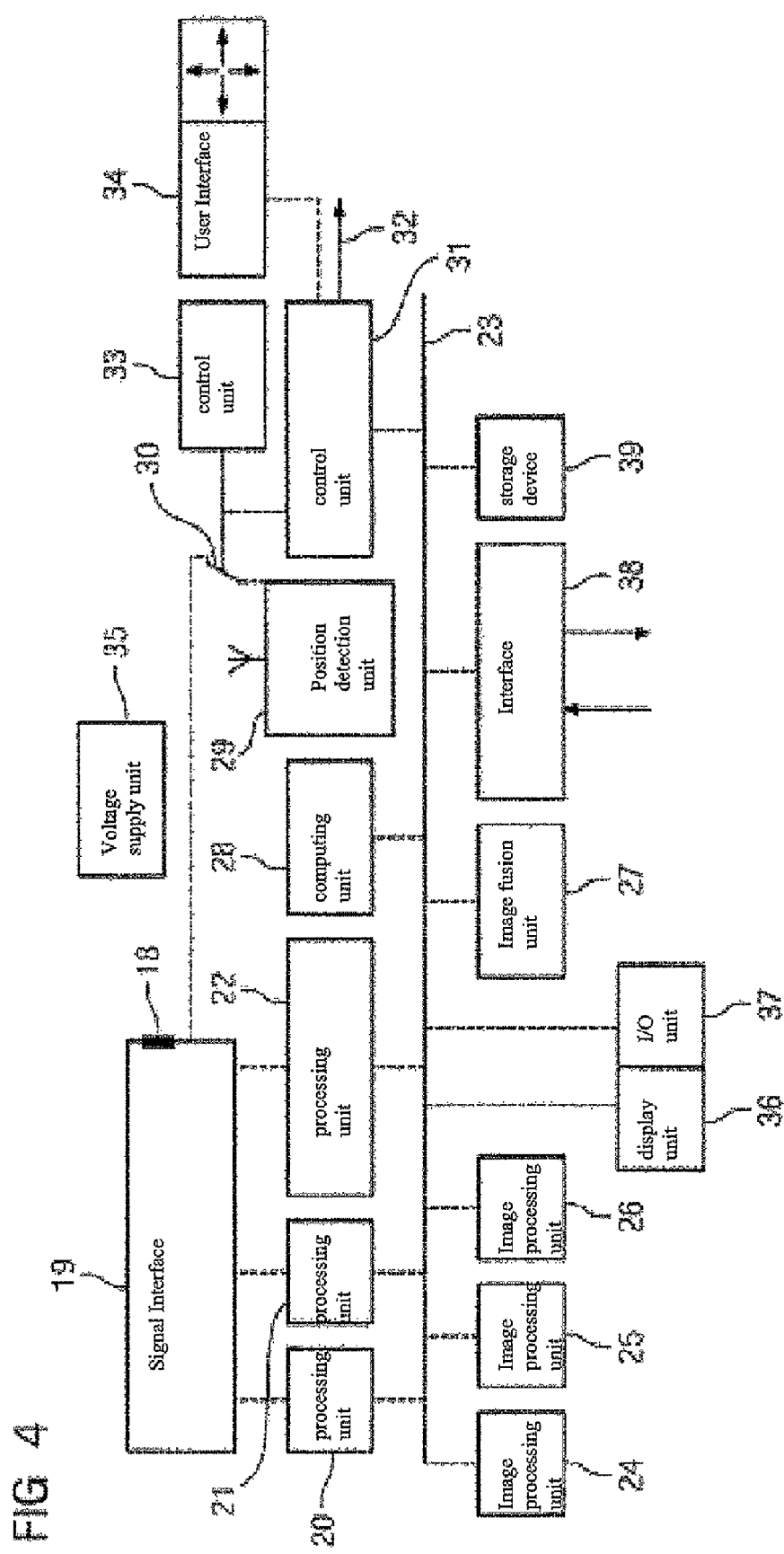

MEDICAL SYSTEM FOR EXAMINATION OR TREATMENT

CROSS REFERENCE TO RELATED APPLICATIONS

This application claims priority to the German application No. 10354496.8, filed Nov. 21, 2003 and which is incorporated by reference herein in its entirety.

FIELD OF INVENTION

The invention relates to a medical examination system and/or treatment system, having a catheter with at least one sensor connected to an image recording system, said sensor being connected to an image processing unit for evaluating the sensor signals recorded in an examination area, a display unit for displaying the images of the image processing unit and a means for determining the position and/or orientation of the catheter tip, whereby the system comprises means for generating three-dimensional images from the two-dimensional images of the image recording system, on the basis of the detected position and/or orientation of the catheter tip.

BACKGROUND OF INVENTION

Vascular diseases, particularly heart attacks, rank among the most frequent diseases which result in loss of life. This is caused by diseases in the coronary vessels (Arteriosclerosis). Deposits of what are known as arteriosclerotic plaque cause a "blockage" in the coronary vessels. The latest findings show that the risk of suffering a heart attack is not mainly due to the reduction in the vessel diameter, but depends much more on the stability of the thin protective layer covering the arteriosclerotic deposits. If this layer breaks down, the platelets are drawn together causing the vessel to be completely closed within a short amount of time, consequently resulting in a heart attack.

SUMMARY OF INVENTION

Examinations into coronary vessels within the framework of coronary angiography have hitherto been carried out essentially by means of cardiac catheter examinations using contrast means with X-ray examinations. This method nevertheless is disadvantageous in that only the vessel diameter which can be used by the blood flow and/or the stenosis is displayed as a silhouette. Information regarding the arteriosclerotic deposits, such as their thickness or the presence of inflammations is thus not possible.

Using another method, an intravascular ultrasound (IVUS) catheter is inserted into the coronary vessel with the aid of a guide wire, and is subsequently removed at a defined speed from the vessel either by hand or by a powered extractor. A method of this type is described in the publication DE 198 27 460 A1. The catheter provides ultrasound images of the coronary vessels, whereby the vessel wall is mostly displayed in a 360° cross-section. These images provide important medical information regarding deposits, such as the presence of inflammation sources or the thickness of the deposits. It is disadvantageous however, that the resolution of the ultrasound images is limited, and that these images only generate a two-dimensional display.

Using a further new method which has already been tested and described in WO 01/11409 A2, an intravascular catheter for optical coherence tomography (OCT), which operates with infrared light, is inserted into the coronary vessel. The images of the OCT system provide additional medical information regarding the arteriosclerotic plaque. This solution is advantageous in that structures in the vicinity of the vessel surface can be displayed with very high detail resolution, microscopic tissue displays being possible to some extent. The disadvantage of this method lies in the low resolution of tissue positioned deeper within the body.

An examination system according to the preamble of claim 1 is known from DE 100 51 244 A1. Position sensors are provided to enable a location of the catheter tip in the body without using X-rays. This method has however not gained acceptance since the insertion of the catheter into the vessel can result in vascular perforations. As a precaution, the insertion of the catheter is always carried out using X-ray examination.

A further disadvantage of known examination and/or treatment systems is that the sensor is not generally positioned in the center of the vessel, but for example, at the edge, thereby resulting in movement artifacts.

An underlying object of the invention is thus to design a medical examination and/or treatment system having an improved image quality without movement artifacts.

This object is achieved by the claims.

With the system according to the invention, three-dimensional images are generated based on two-dimensional images, whereby the respective coordinates of the catheter tip are used as additional information. More realistic images can be generated by incorporating the position data, which allows an improved diagnosis in contrast to conventional systems. In particular, artifacts can be clearly reduced or even completely avoided using 3D images.

The inventive system can be improved further if the means for gene rating the three-dimensional images comprise a computing unit for calculating at least one geometric parameter of the examination area based on the detected position and/or direction of the catheter tip. A relationship can be established between the images and the coordinates of the catheter tip on the basis of this geometric parameter, thus enabling the three-dimensional examination area to be displayed in a more realistic manner. In contrast, only two-dimensional views can be generated using conventional examination systems, since the momentary position of the catheter within a vessel is not taken into consideration.

With the medical examination system and/or treatment system according to the invention, it is particularly practical if the center line and/or the envelope curve of the examination area can be calculated as geometrical parameters. A three-dimensional model of the examination area can be generated using these calculated geometrical parameters, wherein the individual images are precisely arranged. One particularly large advantage can be seen in that based on the at least one calculated geometrical parameter, an offset correction of the two-dimensional image can be implemented. One offset correction is expedient for instance, if the catheter is located in a relatively large vessel in comparison to itself, and is not guided precisely along the centerline of the vessel. In order to achieve as realistic as possible a representation of the examination area in this case, the two-dimensional images in the image plane are corrected using the detected position and/or the direction of the catheter tip.

An offset correction is provided in accordance with the invention which is dependent on the deviations of the two-dimensional images of the geometric parameter, whereby the geometric parameter has the function of a target value. Provision can thereby be made for the offset correction to comprise moving the image in the image plane. Alternatively or in addition it is also possible that the offset correction comprises a rotation of the image, whereby the longitudinal axis of catheter is expediently used as an axis of rotation. Naturally it is also possible that the offset correction comprises a rotation around an axis positioned perpendicular to the longitudinal axis of the catheter as an axis of rotation. The individual corrections described can naturally also be implemented together, for instance if the image is to be moved in the plane and the catheter tip simultaneously deviates from the centerline so that one or a plurality of rotations are necessary.

With the system according to the invention, the three-dimensional images can be generated in the image processing unit which is provided for evaluating the sensor signals of the image recording system. Alternatively however, a second or a further image processing unit can also be provided for generating three-dimensional images comprising hardware means and/or software means.

A sensor for optical coherence tomography can be used as a sensor in the image recording system. A sensor of this type comprises an optical fiber via which light is guided and emitted in the area in which the catheter tip is inserted in the examination area, said fiber guiding reflection light from the illuminated examination area to a first image processing unit.

The use of a sensor of an intravascular ultrasound image recording system as a sensor of the image recording system is also possible however, said sensor emitting and receiving acoustic impulses which are conveyed to one of or the image processing unit as an electrical signal.

The use of a fluorescent optical catheter is also possible, similarly combinations of the different catheters described are also conceivable, an OCT IVUS catheter being particularly preferable.

According to a further development of the invention, it can be provided that means for detecting the position and/or orientation of the catheter tip comprise at least one position sensor arranged in or on the catheter, and interacting with an external detector, or a detector arranged in or on the catheter, and interacting with an internal position sensor.

It is particularly preferable thereby that a plurality, preferably three position sensors are used to detect the position and/or orientation of the catheter with respect to a three-dimensional coordinate system. To this end, the position sensors can preferably comprise transmission coils arranged orthogonally to each other, which interact with assigned receiver coils in the detector. Alternatively the position sensors can have receiver coils which interact with assigned transmission coils arranged in the position detector.

A further improvement to the examination and/or treatment system according to the invention can be achieved if at least one element generating a magnetic field and a device for generating an external magnetic field used for the movement of the catheter inserted into a patient is provided in the area of the catheter tip. This so-called magnetic navigation enables the catheter tip to be moved from the outside in order to achieve a larger number of measuring points, whereby the points at which the catheter tip touches the vessel wall are of particular relevance.

BRIEF DESCRIPTION OF THE DRAWINGS

Further advantages and details of the invention emerge from the exemplary embodiment below, with reference to the drawings, in which:

FIG. 3 shows the insertion of the catheter into a vessel, and FIG. 4 shows the structure of the examination and/or treatment system according to the invention in a schematic representation

DETAILED DESCRIPTION OF INVENTION

Figure 1:
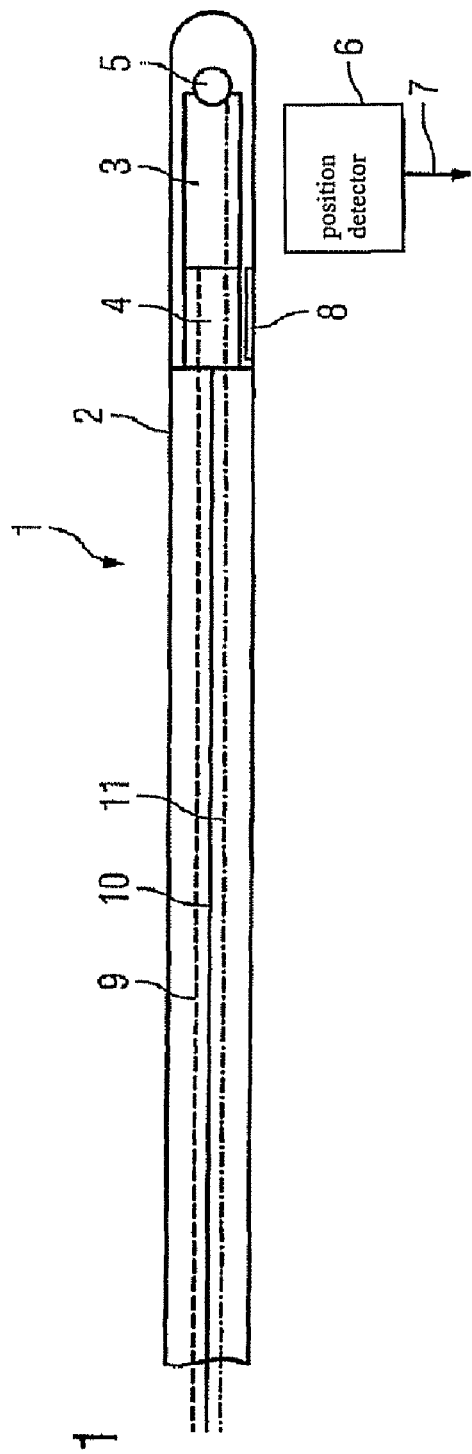
FIG. 1 shows an exemplary embodiment of a catheter of the examination and treatment system according to the invention

The catheter 1 shown in FIG. 1 essentially comprises a catheter shell 2, an IVUS sensor 3 arranged in the area of the catheter tip, which is a part of an intravascular ultrasound image recording system, and an OCT sensor 4, which is a part of an image recording system for optical coherence tomography. In addition, a position sensor 5 is arranged in the catheter 1 in the area of the catheter tip, said position sensor 5 interacting with a position detector 6 located outside the body under examination. The position detector 6 is connected to a position detection unit by means of a schematically represented interface 7. The arrangement of the position sensor and the position detector can also be exchanged so that the position detector is positioned in the catheter and the position sensor is positioned outside the body under examination.

The catheter shell 2 accommodating the sensors 3, 4, 5 is transparent for ultrasound. The IVUS sensor 3 is configured such that the ultrasound is emitted and received in a lateral direction. Since the IVUS Sensor 3 rotates at a high rotation speed, it produces a 360° cross-sectional image of the vessel to be examined. The reflected and received acoustic waves are converted into electrical signals by the IVUS sensor 3, said signals being routed to a signal interface and further to a preprocessing unit and an image processing unit by means of a signal line 9.

The OCT sensor 4 is similarly aligned to the side and generates a continuous image of the vessel to be examined. In the area of the OCT sensor 4, the catheter shell 2 is provided with a viewing window 8 for the infrared light emitted by the OCT sensor 4. The reflected light is guided to a signal interface and further to a preprocessing unit and an image processing unit via a signal line 10 configured as an optical fiber line.

The schematically represented position sensor 5 can also be attached to another location in the area of the catheter tip, behind the OCT sensor 4 for example. The position sensor 5 contains a plurality of electromagnetic units which are configured as transmission coils, whereby a transmission coil is provided for each direction in a three-dimensional coordinate system. The position sensor 5 is connected to the signal interface by means of a signal line 11.

Figure 2:
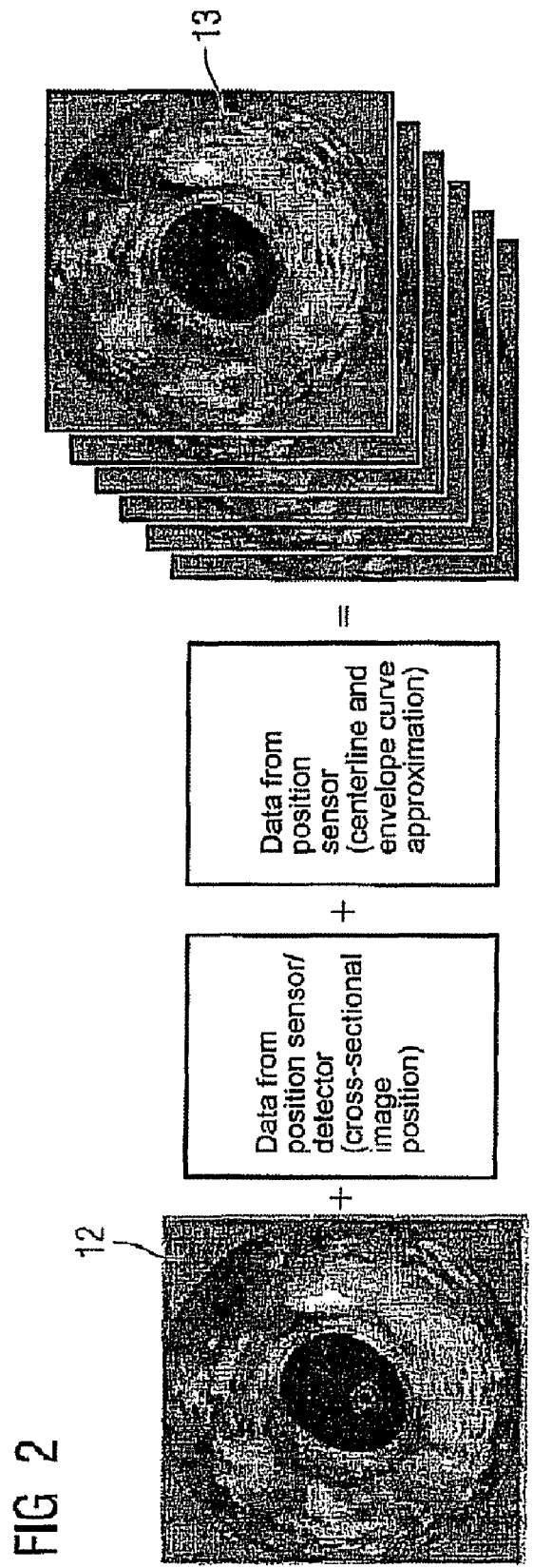
FIG. 2 shows the basic process of the image processing

FIG. 2 shows the basic process of the image processing.

The image 12 generated by the IVUS sensor 3 and the OCT sensor 4 is distinguished by an optimum display in the close-up range and the tissue layers positioned deeper within the body. A plurality of images are recorded- and saved during an examination. The images 12 are combined with the position data detected by the position sensor 5 and the detector 6 associated therewith, so that a position is assigned to each cross-section. The direction of the catheter tip also belongs to this position data, and can be specified by a vector. In the next step, the calculated geometric parameters—centerline and envelope curve—are combined with the sensor positions detected during the image recording to achieve a three-dimensional volume data set. The volume data set 13 comprises a plurality of two-dimensional combined OCT and IVUS images. To generate the three-dimensional volume data set 13, the three-dimensional coordinates of the centerline and the sensor positions detected during the image recording are subtracted from one another. This subtraction corresponds to a three-dimensional movement of the individual two-dimensional images, which are moved in this manner to the calculated centerline. A precise, offset-corrected 3D volume data set is achieved in this manner, wherein artifacts are significantly reduced or even completely eliminated.

In addition to the centerlines further geometric parameters of the vessel can be calculated, which can be used subsequently in further image processing steps. The envelope curve enables the registration of the three-dimensional reconstructed OCT-IVUS images in an interface-based manner with other anatomical image data (MRA, CTA, and 3D-Angio) of the same tissue section and subsequently to display them in a merged manner.

FIG. 3 displays the insertion of the catheter into a vessel.

As shown in FIG. 3, the catheter 1 unavoidably strikes the boundary layers of the vessel during the insertion and movement in a vessel 14. A plurality of boundary points 15,16,17 are achieved in this way, the coordinates of which are determined by means of the position sensor 5. The centerline of the vessel 14 is a one-dimensional line in a three-dimensional space. These can be calculated on the basis of the detected boundary points 15, 16, 17, and can be described by means of a polynomial equation. Similarly, the envelope curve of the vessel 14 can also be determined from the boundary points 15,16,17. One method for reconstructing the centerline and the envelope curve is disclosed in the publication U.S. Pat. No. 6,546,271 B1.

In addition, the minimum and maximum vessel diameter of the examined object can be estimated. It is known that a coronary vessel typically has a diameter of approximately 2 to 9 mm. In this manner, the accuracy of the envelope curve approximation can be improved and the computing expenditure is reduced.

To increase the number of boundary points, at which the catheter tip lies on the vessel wall, the catheter can be moved using magnetic navigation. The position sensor 5 is thus configured such that it can either be used for the position detection of the catheter tip or for magnetic navigation. With magnetic navigation, the catheter tip having position sensor 5 is moved within the vessel by means of a magnetic field applied from the outside.

FIG. 4 displays the structure of the examination and treatment system in a schematic representation.

The catheter 1 is connected to a signal interface 19 by way of the catheter connection 18. The respective signals reach a preprocessing unit 20 for OCT and a preprocessing unit 21 for IVUS via the signal interface 19 for the OCT sensor 4, the IVUS sensor 3 and the position sensor 5. A third preprocessing unit 22 is provided for the signals of the position sensor 5, said signals being used for issuing the 3-D volume data set 13 and the centerline approximation and envelope curve approximation.

The respective data of the preprocessing units 20, 21, 22 reaches an image processing unit 24 for OCT, an image processing unit 25 for IVUS and an image processing unit 26 for generating the 3D-data sets by means of a data bus 23.

The system further comprises an image fusion unit 27, in order to generate a common image from the individual OCT and IVUS images. In addition to a computing unit 28 for the centerline approximation and the envelope curve approximation, a position detection unit 29 is provided for generating the 3D volume data sets. The positions of the catheter tips detected in this manner are transmitted to the computing unit 28 via the data bus 23, so that the centerline and the envelope curve can be calculated.

Switching can be implemented between the position detection unit 29 and a control unit 31 for the magnetic navigation by means of a switch 30. Magnets can be controlled via a schematically displayed interface 32, and effect a movement on the catheter tip. By means of the control unit 33, switching is implemented between the functions as sensor or as electromagnet. In addition, a user interface 34 is provided for the magnetic navigation, and is connected to the control unit 31.

The system further comprises a voltage supply unit 35, a display unit 36 for OCT, IVUS and 3-D images, an I/O unit 37 and an interface 38 for patient information and image data, and an image data storage device 39.

The invention claimed is:

1. A medical system for examination or treatment comprising:
   an image recording device;
   an image processing device for processing sensor signals recorded in an examination area, the examination area being a blood vessel;
   a catheter comprising a first sensor of an imaging system for optical coherence tomography; and a second sensor of an intravascular ultrasound image recording system and a catheter tip, the catheter connected to the image recording system, the first and/or second sensor connected to the image processing device, the catheter further comprising a position sensor or position detector;
   a display device for displaying images generated by the image processing device;
   an external locating device comprising a position detector operatively connected to the position sensor in the catheter, or a position sensor operatively connected to the position detector in the catheter, for detecting a position or an orientation of the catheter tip, wherein the locating device includes a computing unit for calculating at least one geometric property of the examination area based on the detected position or orientation respectively of the catheter tip, the at least one geometric property comprising the centerline and/or an envelope curve of the examination area calculated based on a plurality of boundary points where the catheter strikes a boundary layer of the vessel; and
   a 3D-image generator for generating a three dimensional image using a plurality of two-dimensional images recorded by the image recording device, the 3D-image generator further processing the detected position or orientation respectively of the catheter tip in combination with said at least one geometric property of the examination area for generating the three-dimensional image.

2. The medical system according to claim 1, wherein the geometric property includes an element chosen from the group length, width, height, depth, diameter, volume and shape.

3. The medical examination system according to claim 1, wherein the computing unit is adapted to calculate an offset correction of at least one two-dimensional image based on the geometric property.

4. The medical system according to claim 3, wherein the offset correction includes moving the at least one two-dimensional image in an image plane.

5. The medical system according to claim 3, wherein the offset correction includes a rotation relative to a longitudinal axis of the catheter.

6. The medical system according to claim 1, wherein the offset correction includes a rotation relative to an axis perpendicular to a longitudinal axis of the catheter.

7. The medical system according to claim 1, wherein the system further comprises a further image processing device having hardware means and/or software components for generating the three-dimensional image.

8. The medical system according to claim 1,
wherein the first sensor includes an optical fiber for guiding light to an area adjacent to the catheter tip inserted into the examination area and for guiding reflection light from the examination area to the image processing device.

9. The medical system according to claim 1, wherein the second sensor is adapted to transmit and receive an acoustic impulse.

10. The medical system according to claim 9, wherein the acoustic impulse is fed to the image processing device as an electrical signal.

11. The medical system according to claim 1, wherein the catheter is a fluorescent optical catheter.

12. The medical system according to claim 1, wherein the locating device includes a position sensor arranged in or on the catheter for generating a position signal related to the position or orientation of the catheter tip, the position sensor operatively connected to an external position detector.

13. The medical system according to claim 12,
wherein three position sensors are provided for detecting the position or the orientation of the catheter tip relative to a three-dimensional coordinate system.

14. The medical system according to claim 13,
wherein the position sensors include transmission coils operatively connected to corresponding receiver coils included in the detector.

15. The medical system according to claim 14, wherein the transmission coils are orthogonally arranged relative to each other.

16. The medical system according to claim 1, wherein the locating device includes a position detector arranged in or on the catheter for receiving a localizing signal emitted by an external position sensor.

17. The medical system according to claim 16,
wherein three position sensors are provided for detecting the position or the orientation of the catheter tip relative to a three-dimensional coordinate system.

18. The medical system according to claim 17,
wherein the position sensors include transmission coils operatively connected to corresponding receiver coils included in the detector.

19. The medical system according to claim 18, wherein the transmission coils are orthogonally arranged relative to each other.

20. The medical examination system according to claim 1, wherein the locating device includes a position sensor having a receiver coil, the position sensor arranged in or on the catheter for receiving a position signal related to the position or orientation of the catheter tip, the position sensor operatively connected to an external position detector having a transmission coil for transmitting the position signal.

21. The medical system according to claim 1, further comprising a first magnetic field generator arranged in an area adjacent to the catheter tip for generating a first magnetic field and a second magnetic field generator for generating a second magnetic field interacting with the first magnetic field for moving the catheter inserted into the examination area of a patient within the examination area.

22. A medical system for examination or treatment comprising:
an image recording device;
an image processing device for processing sensor signals recorded in an examination area, the examination area being a blood vessel;
a catheter comprising a first sensor of an imaging system for optical coherence tomography; and a second sensor of an intravascular ultrasound image recording system and a catheter tip, the catheter connected to the image recording system, the first and/or second sensor connected to the image processing device, the catheter further comprising a position sensor or position detector;
a display device for displaying images generated by the image processing device;
an external locating device comprising a position detector operatively connected to the position sensor in the catheter, or a position sensor operatively connected to the position detector in the catheter, for detecting a position or an orientation of the catheter tip, wherein the locating device includes a means for calculating at least one geometric property of the examination area based on the detected position or orientation respectively of the catheter tip, the at least one geometric property comprising the centerline and an envelope curve of the examination area calculated based on a plurality of boundary points where the catheter strikes a boundary layer of the vessel; and
a 3D-image generator for generating a three dimensional image using a plurality of two-dimensional images recorded by the image recording device, the 3D-image generator further processing the detected position or orientation respectively of the catheter tip in combination with said at least one geometric property of the examination area for generating the three-dimensional image.

* * * * *